United States Patent [19]

Takeuchi

[11] Patent Number: 4,476,171
[45] Date of Patent: Oct. 9, 1984

[54] FRAGRANCE RELEASING ARTICLES

[75] Inventor: Keinosuke Takeuchi, Kodoma, Japan

[73] Assignee: Hakugen Co., Ltd., Taito, Japan

[21] Appl. No.: 467,935

[22] Filed: Feb. 18, 1983

[30] Foreign Application Priority Data

Feb. 22, 1982 [JP] Japan .................................. 57-24416
Feb. 22, 1982 [JP] Japan .................................. 57-24417
Mar. 9, 1982 [JP] Japan .................................. 57-37818

[51] Int. Cl.³ .......................... A61K 7/46; A61L 9/04; B44F 1/06
[52] U.S. Cl. ...................................... 428/38; 156/63; 239/60; 239/211; 428/16; 428/28; 428/905
[58] Field of Search .............. 428/28, 38, 905, 15–16; 239/34–60, 211; 156/63; D6/233

[56] References Cited

U.S. PATENT DOCUMENTS

| D. 269,902 | 7/1983 | Edwards .............................. D6/233 |
| 3,619,456 | 11/1971 | Taylor, Jr. ........................ 428/38 X |
| 3,655,493 | 4/1972 | Campbell ............................. 428/38 |
| 4,051,159 | 9/1977 | Tsoucalas et al. ................ 239/60 X |
| 4,293,602 | 10/1981 | Coffey et al. .................... 428/905 X |
| 4,419,395 | 12/1983 | Sugimoto ............................ 428/28 |

Primary Examiner—Henry F. Epstein
Attorney, Agent, or Firm—Bucknam and Archer

[57] ABSTRACT

A fragrance releasing article comprising a frame body with openings into which a fragrance releasing base comprising a resin, perfume and coloring agent is charged; or a fragrance releasing article comprising a resin film with patterns thereon, a frame body and a fragrance releasing base comprising a resin, perfume and, optionally, coloring agent, the film, frame and base being integrally constituted; and a method for producing such articles.

5 Claims, 9 Drawing Figures

FRAGRANCE RELEASING ARTICLES

BACKGROUND OF THE INVENTION

1. Field of the Invention

This invention relates to fragrance releasing articles and a method for producing the same, wherein it is possible to form the article in various shapes and with various patterns and colors appearing on the outer surface thereof.

2. Brief Description of the Prior Art

In the past, fragrant articles have been made by forming a sublimating aromatic material into a specific shape, or by impregnating a perfume into a synthetic resin previously formed into the specific shape.

In those prior aromatic articles, the appearance has been limited by structural factors. For example, the color has been limited to simple colors dictated by the basic coloring of the fragrant material or by the basic coloring of the synthetic resin material. Also, the patterns of those articles have been limited mainly to those applied from the exterior.

Further, as for the method for producing the above-mentioned prior aromatic articles, there have been applied only relatively simple processes, i.e. of forming a specially colored material into a specific shape by means of shaping or molding, or of dipping a previously formed synthetic resin material in a perfume for a given period of time.

SUMMARY OF THE INVENTION

The present invention has been accomplished on the basis of a novel technical idea quite different from the principal idea of the prior art as described above. The inventor of the present invention has succeeded in obtaining improved fragrance releasing articles, compared with the prior aromatic articles, wherein various shapes, pattern and/or colors can be appeared and developed properly on the outer surface thereof, while maintaining a suitable volatility of the fragrant component.

The present invention relates to a fragrance releasing article having a stained glass appearance, comprising a frame formed of thermoplastic or thermosetting resin within which are openings or windows filled with an aromatic base composed of a perfume and coloring agent incorporated into a transparent or semitransparent thermoplastic, or thermosetting resin, said openings corresponding to the colored parts of the design of said article. With the present invention, said article can be obtained by the process of forming a frame of thermoplastic or thermosetting resin having an appropriate number of openings, and separately preparing the fragrance releasing base by the addition to the resin of perfume and colorant; and filling each of the openings with fragrance releasing base of an appropriate color; and heating the article thus obtained at the melting temperature of the resin material for a given period of time, then cooling said body to harden it.

Another embodiment of the present invention relates to fragrant articles with designs, comprising thermoplastic resin-film with the designs photogravured on it, a thermoplastic or thermosetting resin frame provided with openings at the position or positions conforming to the design portions of the film, and a fragrance releasing base which is composed of the transparent or semitransparent thermoplastic, or thermosetting resin which contains the fragrant substance and optional coloring agent, the base covering the film and frame. The article may be obtained by the forming of thermoplastic or thermosetting resin a frame having an appropriate number of openings, and separately preparing the fragrance base by the addition of a perfume and optional coloring agent to a transparent or semitransparent thermoplastic, or thermosetting resin; applying the said fragrance base onto the frame so it adheres to the thermoplastic resin film on which are colored designs; and heating the product thus obtained at the melting temperature of the resin material for a given period of time, then cooling the same so as to harden it.

DESCRIPTION OF THE INVENTION INCLUDING THE PREFERRED EMBODIMENTS

Figure 1:
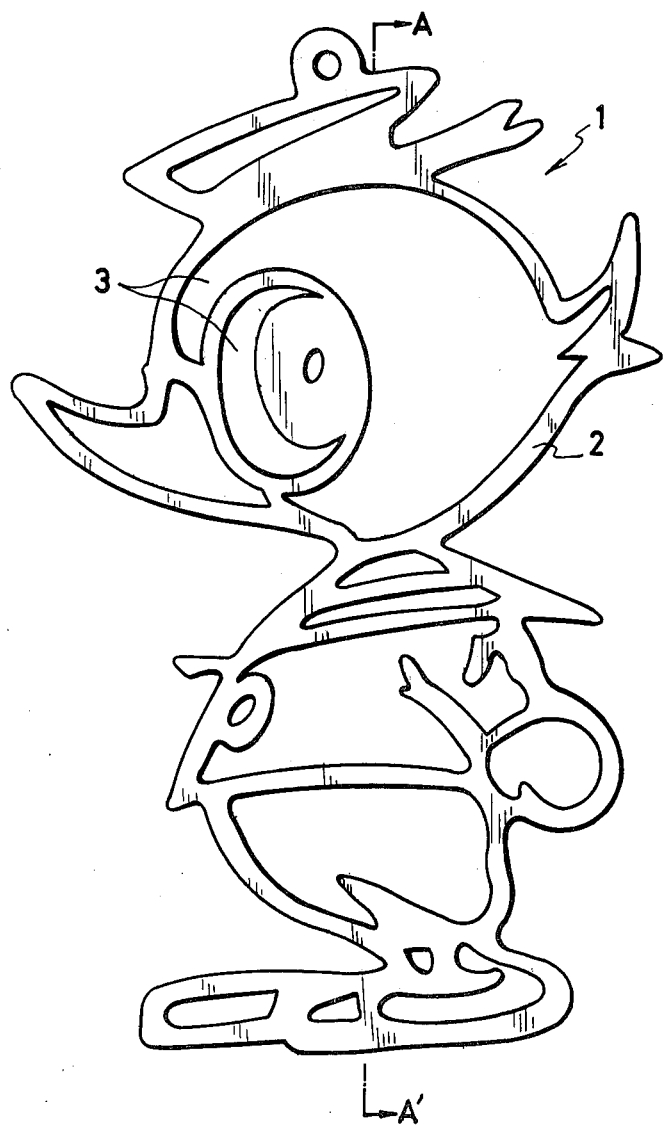
FIG. 1 and FIG. 3 are plan views of fragrance releasing articles having a stained glass appearance in accordance with this invention.

The fragrance releasing article of the present invention is produced by a first step of forming a frame of a desired shape of thermoplastic or thermosetting resin material by commonly known means such as injection molding, extruding, transfer molding, compression molding, cast molding or blanking, punching, or the like, said frame having an appropriate number of openings and preparing the fragrance releasing base as a paste, said fragrance base containing an appropriate amount of perfume and an optical coloring agent added to the transparent or semitransparent thermoplastic resin or the thermosetting resin; a second step wherein each of the openings are fully charged with said paste type fragrance base to which an appropriate coloring agent has been added, in an appropriate coloring arrangement, or a fragrance base with or without the coloring agent added may cover or be deposited on said frame with a thermoplastic resin film carrying colored patterns; and further a third step wherein the body with filled openings or covered by the base or with the base deposited on it is heated to the melting temperature of the material of said fragrance base for a given period of time, and thereafter is cooled to harden it. The above process is referred to as the first production process.

In accordance with the above-mentioned first step, there is formed a frame of an original form with the exterior appearance in the shape of said fragrance releasing article, and in the latter stage thereof, any desired colored fragrance base can be prepared as a paste which can easily be charged into the openings, or the paste covers or is deposited on said frame.

As for the thermoplastic or thermosetting resin used as the materials in the above-mentioned first part of the first step, there may be used materials which do not melt at the predetermined melting temperature in the third step and which are relatively rigid at normal temperature, and preferably which can easily be formed and which adhere to or possess mutual affinity with the above-mentioned fragrance base. As a thermoplastic resin there can be used, for example, polyvinyl chloride, nylon, an olefin resin, a polyethylene terephthalate resin, a polyacrylic resin, a polycarbonate resin or the like. As a thermosetting resin there can be used, for example, a urea resin, a phenol resin, "Bakelite", an epoxy resin or the like.

The frame body to be obtained in such first-part step may in the second step, have the function of a receptacle for the paste type fragrance base, of a partition to separate colors, or of a supporting frame for part of the fragrant base of the fragrant article.

Also, as for the transparent or semitransparent thermoplastic resin or the thermoplastic resin used as the material in the latter stage of the first step, there may be required a material which allows the perfume contained therein to release fragrance after hardening at normal temperature, and preferably said material is chargeable, applicable or depositable in paste form at a relatively low temperature. For example, such materials include transparent and semitransparent thermoplastic resins such as polyvinyl chloride, nylon, olefinic resins, polyester resins (e.g. polyethylene terephthalate resin), acrylic resin, polycarbonate resin and the like; and thermosetting resins such as urea resin, phenol resin, "Bakelite", epoxy resin and the like. Polyvinyl chloride and nylon are preferable. If polyvinyl chloride is used a paste can be obtained by dispersing finely divided particles thereof into a plasticizer and a diluent.

Further, as for the perfume to be added in the latter part of said first step, it is necessary that it does not volatize or decompose when subjected to the predetermined temperature of the third step. For example, when the resin material of the fragrance base is polyvinyl chloride, the perfume may include linaloe oil, rose wood oil, coriander oil and the like each having linalool as the principal component; geranium oil, eucalyptus oil, rose oil, citronella oil, palmarosa oil and the like each having geraniol as the principal component; also mint oil having l-menthol as the principal component; and the like. Also, the perfume may be a mixture of the above. It should be understood that the perfume may be appropriately selected and used so as to provide the fragrance required by the customers. Such perfumes are miscible with the plasticizer and are mixed with it. Therefore, the content of the perfume, in other words the duration of fragrance thereof is controlled by the amount of plasticizer contained in the resin. Accordingly, when the fragrance is required to be maintained for a long period, the fragrance base includes a large amount of plasticizer and becomes soft, while the material of which the frame is composed in the above embodiment does not include perfume, and therefore the amount of plasticizer may be decreased as occasion demands. Thus the frame can be constituted to be relatively rigid. Though it is possible to include the perfume in the material of the frame, when the frame is of the rigid type, the duration of fragrance is relatively short compared with that in the case of the soft type.

Figure 2:
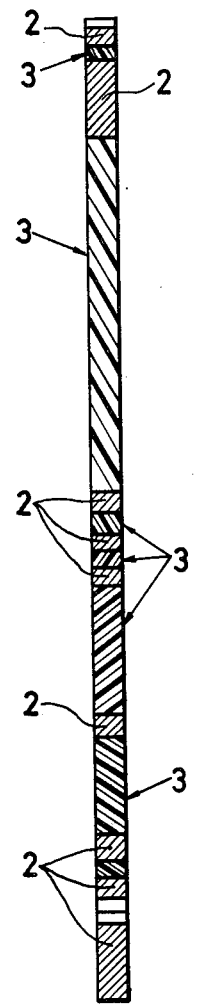
FIG. 2 and FIG. 4 are vertical cross-sections taken along lines A—A' of FIG. 1 and FIG. 3.

Next, in the second step, the paste-type fragrance base is charged in the openings of the above described frame body or is charged or deposited on or covers the frame body. The products obtained by charging such paste-type fragrance base into each of openings of said frame are shown in FIG. 1, FIG. 2, FIG. 3 and FIG. 4. In FIG. 1 and FIG. 2, the fragrant article 1 (symbol 11 in FIGS. 3 and 4) has been achieved by separately preparing the fragrant bases colored by adding suitable coloring agents in the preparation step thereof, and charging and filling said various colored fragrant base of paste type properly into each of openings 3 (symbol 13 in FIGS. 3 and 4) according to the coloring arrangement of the article.

Fragrance releasing articles having various shapes, patterns and colors may be provided by suitably combining frames and various fragrance paste bases of different colors.

An article in the frame of which the paste type fragrance base is deposited or adhered is shown in FIGS. 5, 6, 7 and 8.

Figure 5:
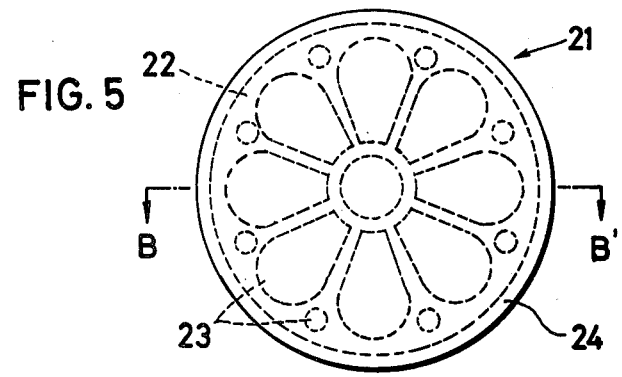
FIG. 5 and FIG. 7 are plan views of the fragrance releasing article having designs, prepared in accordance with this invention.
Figure 6:
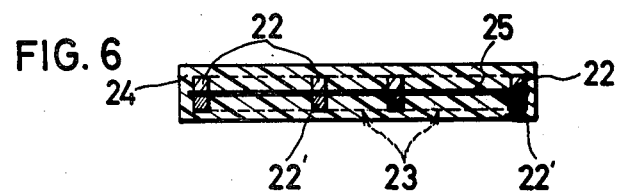
FIG. 6 and FIG. 8 are vertical cross-sections taken along lines B—B' in FIG. 5 and FIG. 7.

In FIGS. 5 and 6, the fragrance releasing article 21 (31 in FIGS. 7 and 8) may be obtained by adhering the thermoplastic resin film 25 (35 in FIGS. 7 and 8), on which the appropriately colored patterns have been previously printed, onto frame body 22' (32 in FIGS. 7 and 8) and onto the other frame body 22' (32' in FIGS. 7 and 8) so that the film 25 is sandwiched between the frame bodies 22 and 22' which are to be stuck together, and depositing the transparent (or semitransparent) fragrance releasing base onto the frame bodies and film so as to cover the film with the base material.

Then, in the third step, the frame body thus filled is heated at the melting temperature of the resin material of said fragrance base for a given period of time so the base melts with the frame and adheres to the film, and thereafter is cooled to harden it. It is necessary that the temperature at which this is done is such that the perfume contained in the fragrance base does not volatilize. For example, when perfume having linalool. (boiling point: 197°–199° C.) as its principal component is used and polyvinyl chloride is used as the resin material of the paste type fragrance base, a temperature of 160°–180° C. may be employed for the heating. When nylon is used as the resin material of the paste type fragrance base, a temperature of 150°–180° C., which is relatively low for this third step, may be employed for the heating. After being thus heated and then cooled, the fragrance base will become hard when at the normal temperature. Fragrant articles with pattern can be formed thus, including those in which the fragrance base portion is integrally fused or bonded to said frame.

The fragrance releasing article of this invention may be also produced according to the second method to the described below.

The method comprises a first step in which the frame body is prepared according to the same method as above, and a second step in which by using a transparent or semitransparent thermoplastic material, or thermosetting resin having an appropriate type and amount of perfume and, if required, with coloring agent contained therein, colored or non-colored fragrance base pellets can be formed, enabling the fragrance base to be applied using various kinds of molding machine, enabling molding such as injection molding at the forming temperature so that the fragrance base pellets may be charged into the openings of the frame to provide a color arrangement, or in the case of frame bodies provided with thermoplastic resin film with colored patterns, colorless fragrance base pellets may be used for covering them, as well as colored ones. In the above second step, conventional multicolor injection molding machines may be employed for charging the said frame openings with the fragrance base and several molding machines may be employed for the bodies.

Further, as the forming temperature may be the temperature according to the melting temperature of the fragrance base pellet material, the relationship between the transparent or semitransparent thermoplastic material, or thermosetting resin material used in the second step for producing the fragrance base pellets, and the perfume used is the same as described in the first method.

As described above, according to such second method, it is possible to produce the fragrant article of this invention by means of conventional injection molding machines and the like in the same way as ordinary synthetic resin molded or formed articles are produced.

As above, the fragrant article of the present invention can be obtained in various shapes, patterns and colors by means of simple processes, the fragrance base thereof being fixed by melting or adhering to the frame. The frame has the function of separating the patterns or colors, as well as of protecting the fragrance base contained in each opening and adhered to the frame and film, and, further, the frame is useful for maintaining the normal shape of the article. Furthermore, the frame may be used to hold the patterned thermoplastic resin film under tension to thus keep the film in the proper shape and form. The materials used for the frame, fragrance releasing base and patterned film may all be the same kind of resin or may differ one from the other. Use of the resins mentioned is preferable because of their good mutually adhesive properties and the tendency to have other similar physical properties in common (e.g. coefficient of expansion). Various resins may be selected if required depending on the purpose for this invention.

The fragrance releasing article according to this invention is preferably in the form of a flat plate, with patterns etc. being formed in the plate and appearing on the surface thereof. However, as is self-evident for those skilled in the art, it may also be formed in other solid shapes, should the purpose to which the article is to be put so requires.

A flat plate type article according to this invention may be utilized in various ways: it may be downed dangled or hung, set in close contact with a wall or glass surface, while it is also possible to use it as a table-cloth and for similar such applications. The fragrant article therefore can also be ornamental in function, as a picture, and thus comes to possess a correspondingly great utility.

Following are examples of this invention. These are presented for explanatory purposes and are not to be considered as limiting the invention in any way.

EXAMPLE 1

A frame body 2 was formed, by the injection molding technique, of polyvinyl chloride resin comprising polyvinyl chloride (100 parts by weight), dibutyl phthalate as plasticizer (30 parts by weight) lithium stearate as stabilizer (2 parts by weight) and a small amount of coloring agent. Also, a fragrance base paste (100 parts by weight) was prepared by incorporating perfume (10 parts by weight) comprising linaloe oil, eucalyptus oil, mint oil, etc., and the diluent into the finely divided particles of polyvinyl chloride resin composed of polyvinyl chloride (100 parts by weight) dibutyl phthalate as plasticizer (60 parts by weight), lithium stearate as stabilizer (2 parts by weight) and a very small amount of coloring agent and the mixture agitated. The required number of such fragrance bases was prepared in accordance with the number of colors of the end product. The frame 2 was then placed in close contact with a flat mirror plate, and the colored fragrance releasing base paste was poured into the openings 3 in accordance with the predetermined color arrangement. Next, the body thus filled was heated in an oven at 180° C. for about 20 minutes, and was then set by cooling, producing the product 1.

Figure 3:
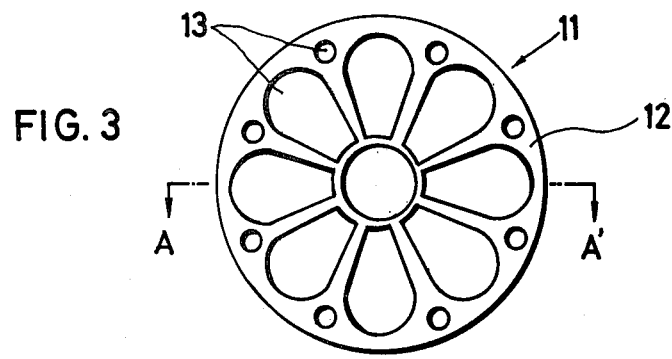
Figure 4:
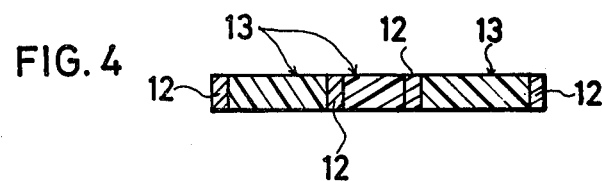

The fragrance releasing article 11 shown in FIGS. 3 and 4 was obtained in the same way. In FIGS. 3 and 4, 12 is the frame body and 13 is the openings.

EXAMPLE 2

Using the same process as in the above Example 1, the frame sides 22 and 22' of the same shape were formed. A polyester film 25 on which colored pattern had been printed was stuck onto the frame side 22 and the frame side 22' was placed on the frame side 22 to thereby hold the film 25 therebetween, providing a frame body with pattern. 100 parts by weight of polyvinyl chloride resin pellets composed of polyvinyl chloride (100 parts by weight), dibutyl phthalate as plasticizer (60 parts by weight), lithium stearate as stabilizer (2 parts by weight) were prepared containing 10 parts by weight of perfume comprising linaloe oil, eucalyptus oil, mint oil, etc. Injection molding was carried out at a forming temperature of 180° C. to deposit polyvinyl chloride resin onto film 25, frames 22 and 22' to thereby obtain the product 21, the openings 23 being filled with the fragrance releasing base. The patterns and colors appearing on the surface of the product are those patterns and colors of the film 25, as portion 24 is a transparent fragrance base.

Figure 7:
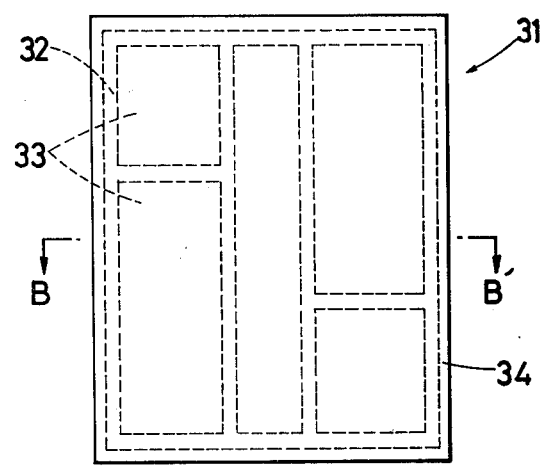
Figure 8:
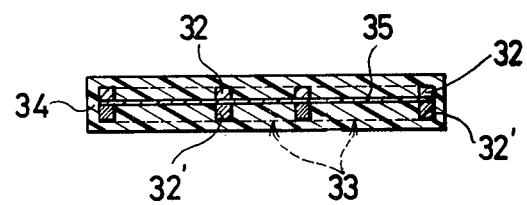

Another fragrance releasing article 31 shown in FIGS. 7 and 8 was obtained in the same way as the above process. In the drawings, 32 and 32' are a frame body, 33 is openings, 34 is a transparent fragrance releasing base portion and 35 is a polyester film with color patterns.

Moreover, the fragrance releasing articles 1, 11, 21 and 31 which were obtained as per the above Examples 1 and 2 maintained their fragrance for more than one month. This was tested as follows. Each article was put in a closed box (0.7 m$^3$) which was maintained at 30° C. After a given period, measured in days, the box was open and the article removed, and a skilled panel of five persons judged whether the article still possessed the fragrance or not. The panel found that all the articles possessed fragrance even after one month.

Figure 9:
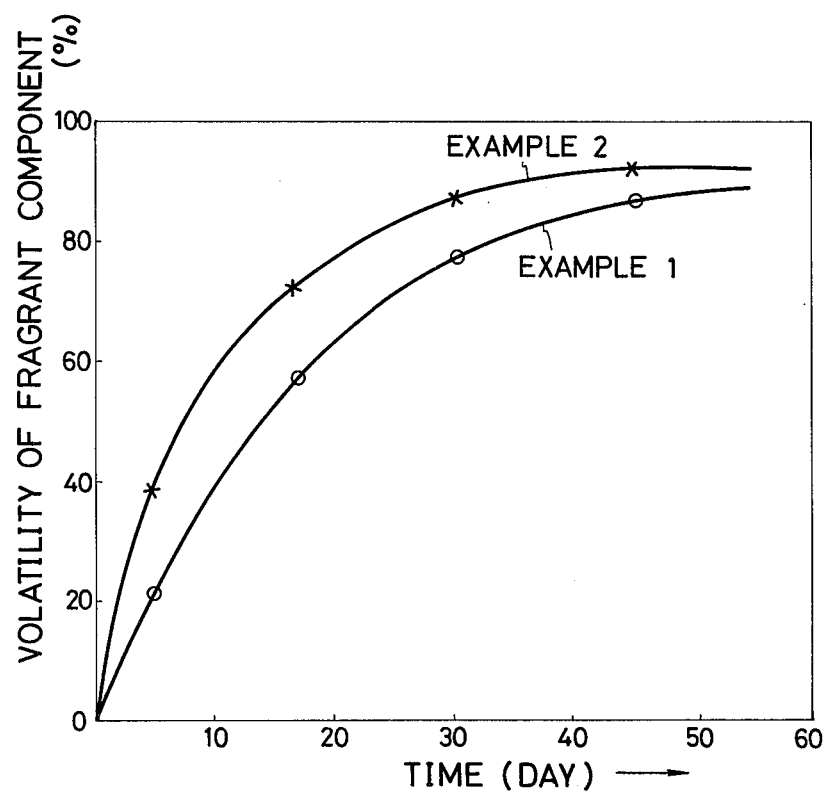
FIG. 9 is a graph showing the change of the volatility with time of the fragrance component.

Furthermore, in order to show the relationship of the change in volatility of the fragrance component with the length of time (in days), the following experiment was carried out. Articles 1 and 21 of Examples 1 and 2, respectively, were put in a closed box (0.7 m$^3$) kept at 30° C. After a certain period as shown in FIG. 9, the box was open, and the test sample removed and weighed. Volatility was estimated as follows.

Volatility (%) =

$$\frac{\text{Volatilized amount of fragrance component}}{\text{Amount of fragrance component used}} \times 100$$

FIG. 9 shows that the articles maintained their fragrance for more than one month.

What is claimed is:

1. A fragrance releasing article comprising a thermoplastic resin film with patterns thereon, surrounded by a frame body formed of thermoplastic or thermosetting resin, a fragrance releasing base comprising a transparent or semitransparent thermoplastic resin or a thermosetting resin, perfumes, said film, frame body and fragrance base being integrally constituted so that said frame body is adhered to said film and said fragrance base adheres to said film and frame body.

2. The article according to claim 1, which said fragrance releasing base additionally contains a coloring agent.

3. The article according to claim 1, wherein said thermoplastic resin and said transparent or semitransparent thermoplastic resin are the same or different, each of them being a member selected from the group consisting of polyvinyl chloride, nylon, olefinic resins, polyester resins, polycarbonate resins and polyacrylic resins, and said thermosetting resin is a member selected from the group consisting of urea resins, phenol resins, Bakelite and epoxy resins.

4. The article according to claim 1, wherein said patterns are photogravured on the thermoplastic resin film.

5. The article according to claim 1, wherein openings are provided in said frame body corresponding to the patterns on said thermoplastic resin film.

* * * * *